United States Patent
An et al.

(10) Patent No.: US 7,851,657 B2
(45) Date of Patent: Dec. 14, 2010

(54) SYNTHETIC PROCESS FOR ANTICANCER DRUG FLUORAPACIN AND TRISULFIDE DERIVATIVES

(75) Inventors: Haoyun An, Carlsbad, CA (US); Xiaopeng Mo, Zhejiang Province (CN)

(73) Assignee: Acea Biosciences, Inc., San Diego, CA (US)

( * ) Notice: Subject to any disclaimer, the term of this patent is extended or adjusted under 35 U.S.C. 154(b) by 0 days.

(21) Appl. No.: 12/413,385

(22) Filed: Mar. 27, 2009

(65) Prior Publication Data

US 2010/0191016 A1 Jul. 29, 2010

Related U.S. Application Data

(63) Continuation of application No. PCT/CN2009/000098, filed on Jan. 23, 2009.

(51) Int. Cl.
C07C 321/00 (2006.01)
(52) U.S. Cl. ..................................................... 568/24
(58) Field of Classification Search ........................ None
See application file for complete search history.

(56) References Cited

U.S. PATENT DOCUMENTS

2005/0261321 A1 11/2005 Xu et al.

FOREIGN PATENT DOCUMENTS

WO WO-2005/112933 12/2005

OTHER PUBLICATIONS

An et al., {Synthesis and anti-tumor evaluation of new trisulfide derivatives, Bioorganic & Medicinal Chemistry Letters (2006), 16(18), 4826-4829}.*
Stensaas et al., {Competitive oxidations of dibenzyl trisulfide vs. substituted aryl polysulfides, Journal of Sulfur Chemistry (2008), 29(3-4), 433-443}.*
Wong et al., {Desulfurization of bibenzyl trisulfide by [CpMo(CO)3]2: Formation and isolation of thiolato-bridged dimolybdenum complexes of [CpMo(CO)2(SBz)]2, [CpMo(CO)(SBz)]2S and [CpMo(SBz)S]2 (Cp = (h5-C5H5), Bz = PhCH2-). Crystal structures of two polymorphs of [CpMo(SBz)S]2, Inorganica Chimica Acta (2007), 360(9), 3113-3118}.*
An et al., Bioorg. Med. Chem. Lett. (2006) 16:4826-4829.
An et al., AAPS PharmSciTech (2008) 9:551-556.
Banerji and Kalena, Tetrahedron Lett. (1980) 21:3003-3004.
Derbesy and Harpp, Tetrahedron Lett. (1994) 35:5381-5384.
Harpp et al., Tetrahedron Lett. (1970) 3551-3554.
Harpp et al., Tetrahedron Lett. (1976) 3001-3004.
Mata-Greenwood et al., Anticancer Res. (2001) 21:1763-1770.
Rosner et al., Biochim. Biophys. Acta (2001) 1540:166-177.
Sinha et al., Organometallics (2001) 20:157-162.

* cited by examiner

*Primary Examiner*—Daniel M Sullivan
*Assistant Examiner*—Chukwuma O Nwaonicha
(74) *Attorney, Agent, or Firm*—Morrison & Foerster LLP

(57) ABSTRACT

The invention provides a synthetic and manufacturing process for the preparation of the anticancer drug, fluorapacin, bis(4-fluorobenzyl)trisulfide, and related trisulfide derivatives on large scale. Also provided are processes for the purification and isolation of fluorapacin having high purity and improved stability.

26 Claims, 7 Drawing Sheets

SYNTHETIC PROCESS FOR ANTICANCER DRUG FLUORAPACIN AND TRISULFIDE DERIVATIVES

CROSS-REFERENCE TO RELATED APPLICATIONS

This application is a continuation of International Application No. PCT/CN2009/000098, filed 23 Jan. 2009, designating the United States of America, the contents of which are hereby expressly incorporated by reference in their entirety.

TECHNICAL FIELD

The invention relates to a synthetic and manufacturing process for preparation of the anticancer drug fluorapacin, bis(4-fluorobenzyl)trisulfide, and related trisulfide derivatives.

BACKGROUND ART

Dibenzyl trisulfide (DBTS) is a biologically active polysulfide secondary metabolite isolated from the sub-tropical shrub, *Petiveria alliacea*, L. (Phytolaccaceae) that has been reported to have immunomodulatory and anti-proliferative activity. See, e.g., Rosner et al., *Biochim. Biophys. Acta*, (2001), 1540:166-177; and Mata-Greenwood, et al. *Anticancer Res.* (2001), 21:1763-1770.

Further optimization of this compound led to the discovery of a new anticancer drug candidate, fluorapacin, bis(4-fluorobenzyl)trisulfide. See, e.g., An et al., *Bioorg. Med. Chem. Lett.* (2006), 16:4826-4829. The therapeutic application of fluorapacin as an anticancer drug has been previously described. See, e.g., PCT/US2005/013474 (International Publication WO 2005/112,933); U.S. Ser. No. 11/110,203 (published as US 2005/0261321, now allowed); and CP200580012460.5.

The naturally-occurring antibiotics varacin, lessoclinotoxin A, Calicheamicin and esperamicin derivatives include cyclic or acyclic polysulfide moieties which are critical for biological activities of these natural products. The synthesis of some small molecule polysulfide derivatives has been previously reported. See, e.g., Clennan & Stensaas, *Org. Prep. Proc. Int.* (1998), 30:551-600. However, the methods have seldom been used for the synthesis of biologically active and therapeutically useful compounds.

Harpp and co-workers reported the synthesis of dibenzyl trisulfide (Harpp et al., *Tetrahedron Lett.* (1970), 3551-3554) using the following scheme:

This synthetic route involved several steps and the use of unstable intermediates which resulted in low overall yields.

The same researchers also reported the synthesis of trisulfide derivatives (Harpp & Granata, *Tetrahedron Lett.* (1976), 3001-3004) using the following route:

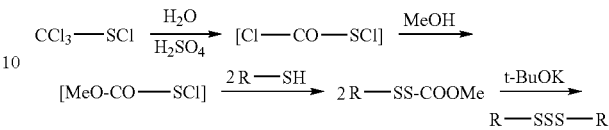

The starting material for this synthesis, $CCl_3-SCl$, is not commercially available and this reagent, as well as the two synthetic intermediates indicated in brackets, is unstable and toxic. Because of difficulty storing and handling the starting material and the intermediates, this route does not appear amenable to large scale synthesis.

The preparation of trisulfides by reaction of diimidazolylsulfide and thiols was described by Banerji & Kalena, *Tetrahedron Lett.* (1980), 21:3003-3004. A modification of this approach was described for the synthesis of trisulfide derivatives, including fluorapacin, on laboratory scale in U.S. Ser. No. 11/110,203.

Roy and co-workers recently reported the synthesis of symmetrical trisulfide derivatives using copper (II) salts and elemental sulfur (Sinha et al., *Organometallics*, (2001), 20:157-162) by the following route:

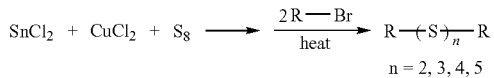

This route produced a complicated mixture of di-, tri-, tetra- and penta-sulfide derivatives, that were difficult to separate from the mixture because of the similar physicochemical properties of these derivatives. In preliminary studies using this approach and a model compound, it proved impossible to isolate the desired trisulfide from the mixture even utilizing HPLC. The partially purified trisulfide product also underwent disproportionation during and after the purification because of the existence of other impurities and polysulfides. Therefore, this approach could not be applied to the large scale synthesis of fluorapacin and related trisulfide derivatives.

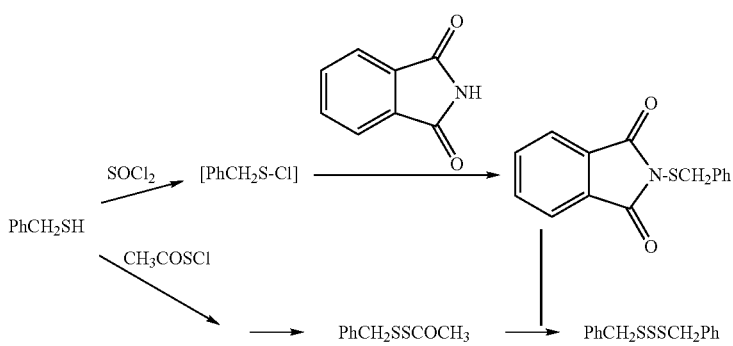

Organo-sulfur compounds, and in particular sulfur chloride (—S—Cl) compounds, have a strong, irritating smell, and are difficult to synthesize. Therefore, the synthesis of organo-sulfur compounds, especially trisulfide derivatives, and their applications in biology, medicine, and other areas have been severely limited. Up to the present, no process has been reported in the literature for the large scale synthesis of trisulfide derivatives.

While a number of workers have reported methods for the preparation of trisulfide derivatives, these routes generally require multiple synthetic steps and/or the formation of unstable, toxic intermediates or starting materials. In addition, many of the literature routes are complicated by the formation of mixtures of products or by-products, making the desired trisulfide derivatives difficult to isolate and purify in good yields. The trisulfide products obtained are frequently unstable when not in highly pure form, and have been observed to undergo decomposition or disproportionation during and after purification due to the presence of impurities. Accordingly, there remains a need in the art for processes suitable for the large scale synthesis and purification of this novel class of biologically active molecule, especially ones that are to be used as drugs, where purity and stability are critical.

Therefore, it is essential to discover and develop an efficient and practical synthetic and manufacturing process for the trisulfides so that new anticancer drug fluorapacin and related trisulfide derivatives can be manufactured in large scale to fulfill the clinical and further development needs. The discovery and development successes of the new anticancer drug fluorapacin [bis(4-fluorobenzyl)trisulfide] also encouraged us to develop an efficient, practical, inexpensive, and safe technological process for large scale synthesis and manufacture of trisulfide derivatives.

DISCLOSURE OF THE INVENTION

The present invention relates to a synthetic route and technological process for the large scale synthesis and manufacture of the anticancer drug, fluorapacin, and related trisulfide derivatives. The present invention also provides processes for the purification and isolation of fluorapacin having high purity, which demonstrates improved stability.

In one aspect, the invention provides a process for preparing a product of formula (I),

R—CH$_2$—S—S—S—CH$_2$—R     (I), said process comprising:
a) providing a solution of N-(trimethylsilyl)imidazole in an organic solvent;
b) adding neat sulfur dichloride to said solution to provide a reaction mixture comprising diimidazolylsulfide; and
c) without isolation, contacting the diimidazolylsulfide with a thiol reagent of formula RCH$_2$SH to provide the product of formula (I);
wherein each R is an optionally substituted aryl or an optionally substituted heteroaryl group.

In another aspect, the invention provides a process for preparing a product of formula (II) (fluorapacin),

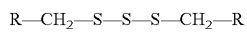

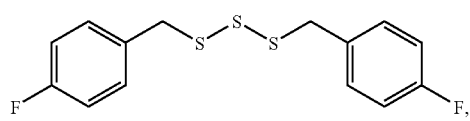

said process comprising:
a) providing a solution of N-(trimethylsilyl)imidazole in an organic solvent;
b) adding neat sulfur dichloride to said solution to provide a reaction mixture comprising diimidazolylsulfide; and
c) without isolation, contacting the diimidazolylsulfide with a thiol reagent of formula (4-F—C$_6$H$_4$)CH$_2$SH, to provide the product of formula (II).

In some embodiments, the process for the preparation of the product of formula (I) or formula (II) further comprises an isolation step d), and may comprise a purification step e), wherein step e) comprises recrystallization of the isolated product from step d) from at least one crystallization solvent, wherein the product of formula (I) or formula (II) is a crystalline product.

In a further aspect, the invention provides a process for preparing crystalline fluorapacin having ≧98% purity, said process comprising:
a) dissolving crystalline fluorapacin in hexanes at a temperature ≦60° C. to provide a hot solution;
b) filtration of the hot solution (e.g., through Celite) to give a filtrate, and warming the filtrate if necessary to provide a clear solution;
c) maintaining the solution at a desired temperature until crystallization occurs, to provide a crystalline product;
d) isolation of the crystalline product (e.g., by filtration), to provide crystalline fluorapacin having ≧98% purity.

In another aspect, the invention provides a process for preparing a fluorapacin sample of high quality and purity, said process comprising:
a) dissolving crystalline fluorapacin in hexanes at a temperature ≦60° C. to provide a hot solution;
b) filtration of the hot solution (e.g., through Celite) to provide a filtrate, and warming the filtrate if necessary to provide a clear solution;
c) maintaining the solution at a desired temperature until crystallization occurs to provide a crystalline product;
d) isolation of the crystalline product (e.g., by filtration), to provide crystalline fluorapacin having ≧98% purity;
e) recrystallization of the crystalline fluorapacin from step d) from hot anhydrous ethanol and then gradual cooling to room temperature under conditions of constant humidity and constant temperature (optionally in a class 100,000 clean room) to provide a crystalline product; and
f) isolation of the crystalline product by filtration, to provide the fluorapacin drug standard having ≧99.5% purity.

In another aspect, the invention provides crystalline fluorapacin having ≧98% purity, preferably ≧99.5% purity, prepared according to one or more of the processes described herein.

The present invention provides a "one-pot two-step" strategy and process for the synthesis of fluorapacin as further described herein. The methods are especially suitable for large scale work because they avoid complex manipulations and chromatographic purification processes.

The present invention is also directed to the technological process for the large scale synthesis and manufacture of fluorapacin as illustrated in FIG. 1.

In one embodiment, the present invention provides optimal molar ratio of the starting materials, reagents, and solvents in above technological processes.

In another embodiment, the present invention also provides a detailed process for further purification and refinement of the product as illustrated in FIG. 2 in order to obtain crystalline fluorapacin that fulfills the purity and quality requirements for a drug standard.

The methods of the present invention are advantageous in terms of the yield and purity of the intermediates and the final products produced therefrom. The methods of the present invention allow the efficient conversion, as well as improved isolation and purification procedures, for the preparation of trisulfide derivatives, in particular the preparation of fluorapacin on large scale. The invention also provides fluorapacin and related trisulfide products having high purity prepared according to the processes described herein.

The technological process described herein for the large scale synthesis of fluorapacin, bis(4-fluorobenzyl)trisulfide, has high generality for similar trisulfide derivatives with two substituted benzyl type or heterocyclic methylene type of moieties at both ends of the trisulfide. Therefore, the present invention also provides a technological process for the large scale synthesis of other symmetrical trisulfide derivatives having two benzylic type (Ar—$CH_2$—) or heterocyclic methylene type (Heterocyclic ring —$CH_2$—) moieties, which are further substituted on the aromatic or heterocyclic rings with one, two, three, four, or five substituents, which may be the same or different, excluding nucleophilic substituents (e.g., OH, SH, and $NH_2$) that can themselves undergo reaction with intermediates of this synthesis.

MODES OF CARRYING OUT THE INVENTION

Figure 1:
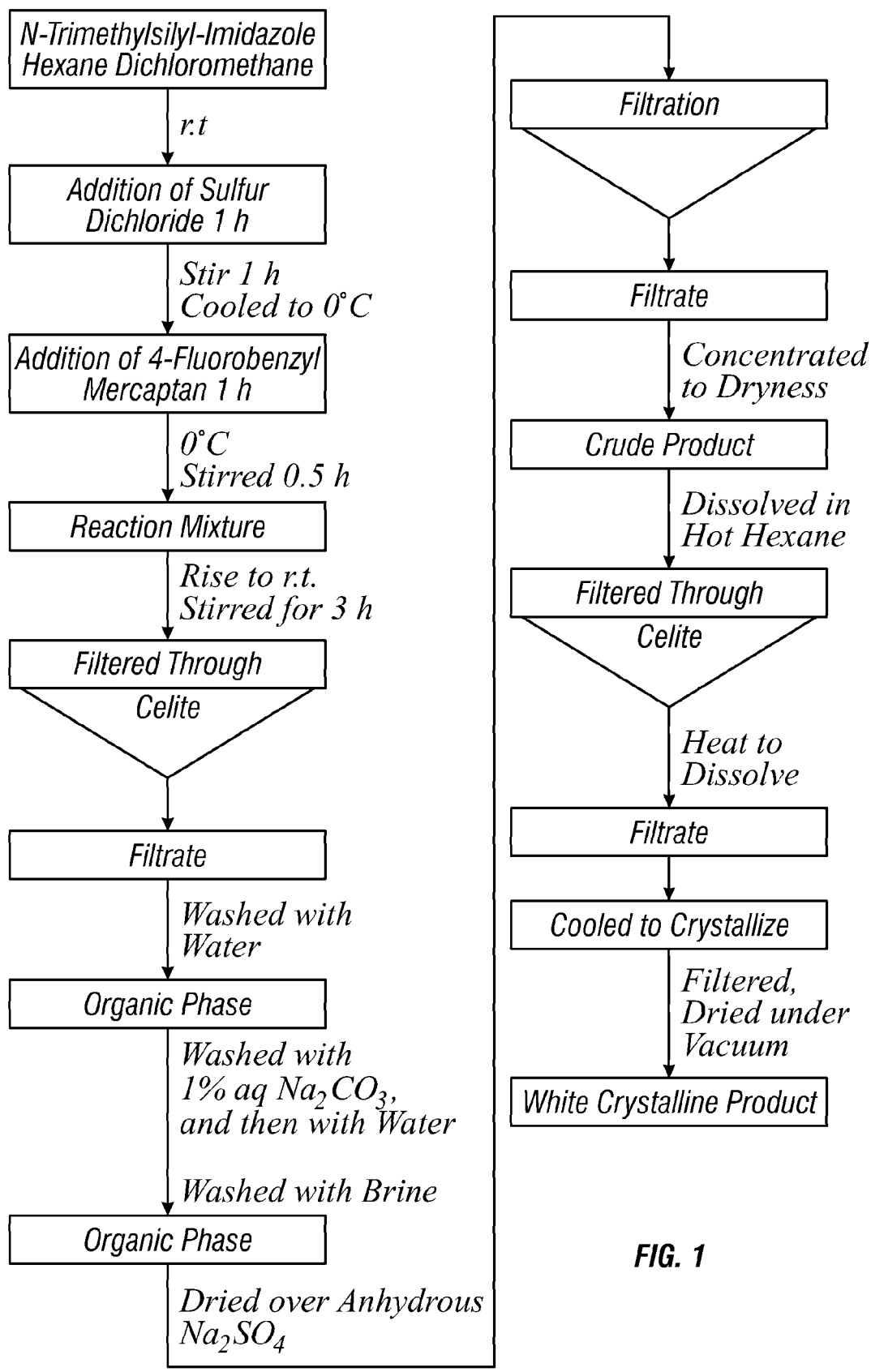
FIG. 1 shows a schematic representation of the technological process and for the large scale synthesis and purification of fluorapacin.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more".

The term "alkyl" as used herein refers to saturated hydrocarbon groups in a straight, branched, or cyclic configuration and particularly contemplated alkyl groups include lower alkyl groups (i.e., those having ten or less carbon atoms). Sometimes, alkyl groups contain 1-10 carbon atoms, sometimes 1-6 carbon atoms, and sometimes 1-4 carbon atoms. Exemplary alkyl groups are methyl, ethyl, propyl, isopropyl, butyl, sec-butyl, tertiary butyl, pentyl, isopentyl, hexyl, etc.

The term "alkenyl" as used herein refers to an alkyl as defined above and having at least one double bond. Thus, particularly contemplated alkenyl groups include straight, branched, or cyclic alkenyl groups having 2-10 carbon atoms, sometimes 2-6 carbon atoms, and sometimes 2-4 carbon atoms (e.g., ethenyl, propenyl, butenyl, pentenyl, etc.). Similarly, the term "alkynyl" as used herein refers to an alkyl or alkenyl as defined above and having at least one triple bond. Especially contemplated alkynyls include straight, branched, or cyclic alkynes having 2-10 carbon atoms, sometimes 2-6 carbon atoms, and sometimes 2-4 carbon atoms (e.g., ethynyl, propynyl, butynyl, etc.).

The term "cycloalkyl" as used herein refers to a cyclic alkane (i.e., in which a chain of carbon atoms of a hydrocarbon forms a ring), preferably including three to eight carbon atoms. Thus, exemplary cycloalkanes include cyclopropyl, cyclobutyl, cyclopentyl, cyclohexyl, cycloheptyl, and cyclooctyl. Cycloalkyls also include one or two double bonds, which form the "cycloalkenyl" groups.

Alkyl, alkenyl, alkynyl and cycloalkyl groups may be optionally substituted with substituent groups suitable for their structure. Examples of optional substituent groups when present on an alkyl, alkenyl, alkynyl or cycloalkyl moiety include, for example, oxo (=O), halo (Cl, Br, F, I), CN, COOH, amide, ester, acyl, alkoxyl, alkylthio, alkylamino, acetylamino, heterocycle, and aryl.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups wherein at least one carbon atom of a corresponding alkyl, alkenyl, or alkynyl group is replaced by N, O or S to form a heteroalkyl, heteroalkenyl, or heteroalkynyl group. Exemplary heteroalkyls include alkoxyl and thioalkoxyl groups, e.g., as —O-alkyl and —S-alkyl, in particular $C_{1-4}$ alkoxyl and thioalkoxyl, secondary and tertiary alkyl amines, and the like.

As used herein, "acyl" encompasses groups comprising an alkyl, alkenyl, alkynyl, aryl or arylalkyl radical attached at one of the two available valence positions of a carbonyl carbon atom, e.g., —C(=O)R where R is an alkyl, alkenyl, alkynyl, aryl, or arylalkyl group, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)$NR_2$ as well as —C(=O)-heteroaryl.

The term "aryl" or "aromatic moiety" as used herein refers to a monocyclic or fused bicyclic moiety having the well-known characteristics of aromaticity, which may be carbocyclic or may further include one or more non-carbon atoms. Thus, contemplated are aryl groups including phenyl, naphthyl, pyridyl, etc. Further contemplated are aryl groups that may be fused (i.e., covalently bound with 2 atoms on the first aromatic ring) with one or two 5- or 6-membered aryl or heterocyclic group, and are thus sometimes termed "fused aryl" or "fused aromatic". Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a C1-C8 heteroalkyl group. These linkers may also include a carbonyl group, thus making them able to provide substituents as an acyl or heteroacyl moieties. "Arylalkyl" groups are described by the total number of carbon atoms in the ring and alkylene or similar linker. Thus a benzyl group is a C7-arylalkyl group, and phenylethyl is a C8-arylalkyl. "Heteroarylalkyl" refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. For example, heteroaryl groups include pyridylmethyl, pyridylethyl, —O-benzyl, and the like.

"Alkylene" as used herein refers to a divalent hydrocarbyl group; because it is divalent, it can link two other groups together. Typically it refers to —(CH$_2$)$_n$— where n is 1-8. "Heteroalkylene" is used to describe the corresponding groups wherein at least one carbon atom of a corresponding alkylene group is replaced by N, O or S. Thus, —C(=O) NH— is an example of a two-carbon substituted heteroalkylene, where N replaces one carbon, and C is substituted with a =O group.

The term "benzyl" as used herein refers to an aryl or aromatic group attached to a methylene (CH$_2$) unit, wherein the aryl group or aromatic group may be further substituted by 1-5 substituents at any position or combination of positions on the aryl or aromatic ring.

As used herein, the terms "heterocycle" and "heterocyclic moieties" are used interchangeably to refer to any compound in which a plurality of atoms form a ring via a plurality of covalent bonds, wherein the ring includes at least one atom other than a carbon atom. Particularly contemplated are heterocyclic moieties including 5- and 6-membered rings comprising nitrogen, sulfur, or oxygen as the non-carbon atom(s) (including, for example, imidazole, pyrrole, pyrazole, triazole, dihydro pyrimidine, indole, pyridine, thiazole, oxazole, tetrazole, etc). The term "heterocyclic-CH$_2$—" or "heterocyclic-methylene" as used herein refers to the heterocyclic moiety, as described above, attached to a methylene (CH$_2$) unit. These heterocyclic moieties may optionally be further substituted by optional substituents.

The term "substituted" means that the specified group or moiety bears one or more non-hydrogen substituents. The term "unsubstituted" means that the specified group bears no such substituents. "Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described.

Aromatic or heterocyclic moieties may be optionally substituted with a variety of substituents, including by way of example and not limitation, halo (i.e., Cl, Br, F, I), CN, COOH, amide, ester, acyl, alkyl, alkenyl, alkynyl, alkoxyl, alkylthio, alkylamino, acetylamino, heterocycle, aryl, etc. Substituents having strong nucleophilicity, such as OH, SH, and NH$_2$, are excluded unless present in protected or masked form (e.g., as an alkoxy, thioalkoxy or in an acylated form). The optional substituent groups described can be selectively substituted at any position or, if more than one substituent is present, in any combination of positions on the aromatic or heterocyclic moiety.

Unless otherwise indicated, the term "oxo" refers to =O.

"Halo", as used herein, includes fluoro, chloro, bromo and iodo. Fluoro, chloro, and bromo are often preferred.

"Amino" as used herein refers to NH$_2$, but where an amino is described as "substituted" or "optionally substituted", the term includes NR'$_2$ wherein each R' is independently H, or is an alkyl, alkenyl, alkynyl, acyl, aryl, or arylalkyl group or a heteroform of one of these groups, each of which may be optionally substituted. The term also includes forms wherein the two R' groups on one nitrogen atom are linked together to form an azacyclic ring. Amino groups may optionally be in a protected or unprotected form.

Selection of Sulfur Transferring Reagent

It was reported that sulfur dichloride (SCl$_2$) can be used as a sulfur transferring reagent to connect two mercaptan molecules together via a nucleophilic reaction, to form a symmetric trisulfide derivative (Derbesy & Harpp, *Tetrahedron Lett.* (1994), 35:5381-5384) (see the scheme below).

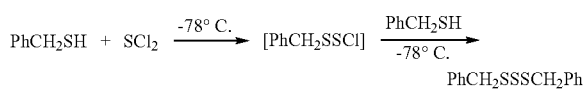

The reaction of benzyl mercaptan with sulfur dichloride in the first step generated benzyl disulfide chloride (PHCH$_2$—SSCl), which is unstable and hard to isolate or handle, and requires extremely low temperature to prevent decomposition of the intermediate. It is difficult to obtain and maintain this low temperature for the large scale synthesis and manufacture of trisulfide derivatives even with very expensive and complicated equipment.

Further literature studies indicated that sulfur dichloride can be converted to relatively stable bis-heterocyclic sulfide derivatives which are still reactive enough to use as sulfur transferring reagents for the reaction in next step. Therefore, harsh or demanding reaction conditions and complicated equipment would not be required to fulfill the large scale synthetic need. See, e.g., Harpp et al., *Tetrahedron Lett.* (1970), 3551-3554, and Banerji & Kalena, *Tetrahedron Lett.* (1980), 21:3003-3004.

Bis-heterocyclic sulfide derivatives, such as di-imidazolyl-sulfide(N,N'-thiodiimidazole), bis[1,2,4]triazolylsulfide(N, N'-thiobis[1,2,4]triazole) or dibenzoimidazolylsulfide(N,N'-thiobenzoimidazole), are expected to meet the requirements mentioned above. By carefully comparing the stability and reactivity of these sulfur dichloride equivalents, diimidazolylsulfide was found to have the most desirable properties as a reactive sulfur transferring reagent in the reactions. Therefore, the following synthetic route was selected and utilized for further development research of the large scale synthesis of fluorapacin (Scheme 1).

Scheme 1. Synthetic Route for Fluorapacin

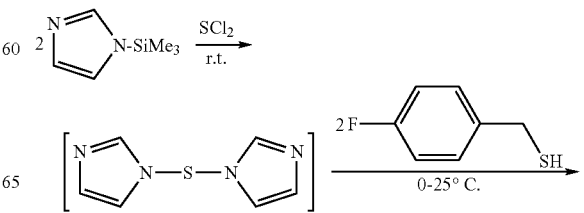

-continued

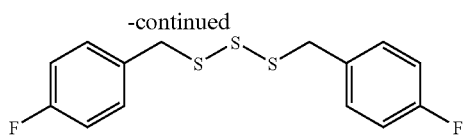

This synthetic strategy requires a minimum number of synthetic steps, and the synthesis can be performed under ordinary conditions without the use of specialized equipment or facilities. The N-(trimethylsilyl)imidazole starting material is easily accessible in various countries. This "one-pot two-step" synthetic strategy was chosen for the large scale synthesis of the symmetrical trisulfide anticancer drug, fluorapacin. The reaction conditions, reagent ratio, technological process, purification and related conditions were all optimized as described in the present invention.

Synthetic and Technological Process

The invention provides synthetic and technological processes useful for the preparation of fluorapacin and related trisulfide derivatives on large scale and having high purity.

In one aspect, the invention provides a process for preparing a product of formula (I),

said process comprising:
a) providing a solution of N-(trimethylsilyl)imidazole in an organic solvent;
b) adding neat sulfur dichloride to said solution to provide a reaction mixture comprising diimidazolylsulfide; and
c) without isolation, contacting the diimidazolylsulfide with thiol reagent of formula $RCH_2SH$ to provide the product of formula (I);
wherein each R is an optionally substituted aryl or an optionally substituted heteroaryl group. The two R groups in formula I are typically the same in these methods.

In some embodiments for the preparation of a product of formula (I), each R group is an optionally substituted phenyl. In some such embodiments, each R is phenyl substituted at any location with one, two or three substituent groups. In other embodiments, each R group is an optionally substituted heteroaryl group. In a preferred embodiment, each R group is (4-fluoro)phenyl.

In another aspect, the invention provides a process for preparing a product of formula (II) (fluorapacin),

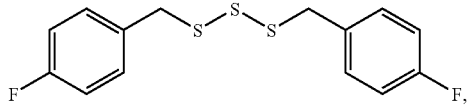

said process comprising:
a) providing a solution of N-(trimethylsilyl)imidazole in an organic solvent;
b) adding neat sulfur dichloride to said solution to provide a reaction mixture comprising diimidazolylsulfide; and
c) without isolation, contacting the diimidazolylsulfide with $(4\text{-}F\text{-}C_6H_4)CH_2SH$, to provide the product of formula (II).

The solvent for each of these methods can be a single conventional organic solvent such as diethyl ether, MTBE, hexanes, heptane, cyclohexane, dichloromethane, carbon tetrachloride, chloroform, dichloroethane, DME, dioxane, THF, petroleum ether, and the like, or a mixture of two or more of these solvents. In some embodiments for the preparation of products of formula (I) or (II), the organic solvent in step a) comprises a halogenated solvent. In some such embodiments, the organic solvent in step a) comprises a mixture of hexanes and dichloromethane. Optionally, the solvent consists of a mixture of dichloromethane and a C5-C10 alkane or mixture of such alkanes. In a specific embodiment, the organic solvent in step a) is a mixture of hexanes and dichloromethane having a ratio of about 3:1.

In some embodiments, the solution in step a) has a concentration of N-(trimethylsilyl)imidazole of about 1.0 moles/L to about 2.2 moles/L. Preferably, the concentration of step a) is from about 1.0 moles/L to about 1.4 moles/L.

In frequent embodiments, the solution of N-(trimethylsilyl)imidazole in step a) is provided at about room temperature. In specific embodiments, the solution in step a) is maintained at a temperature of between about 15° C. and about 30° C., preferably between about 20° C. and about 25° C.

It is important to use neat sulfur dichloride in step b) of the processes described herein, as the use of sulfur dichloride in solution as previously reported provides inferior results. The use of neat sulfur dichloride is advantageous for large scale synthesis because it permits the reaction to be run at a higher concentration and minimizes the amount of solvent required for the process and the solvent waste generated. In addition, the 1.0 M dichloromethane solution used previously proved unstable on storage after initial use, making it difficult to control the amount of reagent used in the reaction, resulting in a decrease in the yield and purity of the reaction product and requiring more extensive purification. In addition, the presence of additional impurities and the increased purification time resulted in additional decomposition of the product before and during purification. The stoichiometry of neat sulfur dichloride is easier to control on large scale, resulting in greater batch consistency and yields for the manufacture of the claimed trisulfides. Neat sulfur dichloride can be repurified if required prior to use, and the repurified material provides the same results and avoids the waste stream generated by disposal of the partially decomposed dichloromethane solution. Therefore, neat sulfur dichloride has the advantages of being easily manageable, resulting in a steady process, consistent yields, and high purity products, and minimizing the waste stream for the large scale manufacture of fluorapacin.

In some embodiments, the neat sulfur dichloride in step b) is added dropwise to the solution of N-(trimethylsilyl)imidazole. The dropwise addition can be accomplished using standard laboratory equipment, for example, via an addition (or dropping) funnel, or by syringe. In some such embodiments, the neat sulfur dichloride is added slowly or dropwise over about 1 hour at room temperature. In certain embodiments, in particular on very large scale, it may be preferable to add the sulfur dichloride in step b) at a rate to maintain internal temp below about 40° C., and preferably below about 30° C.

In frequent embodiments, step c) further comprises cooling the reaction mixture to about 0° C. prior to contacting the diimidazolylsulfide with the thiol reagent. In certain embodiments, the thiol reagent is provided as a solution in an organic solvent. Frequently, the solution of the thiol reagent is added slowly or dropwise to the reaction mixture containing diimidazolylsulfide. In some embodiments, the thiol is provided as a solution in an organic solvent comprising a halogenated solvent. In a specific embodiment, the organic solvent comprises hexanes and dichloromethane, or consists essentially of hexanes and dichloromethane.

In a preferred embodiment, the thiol reagent in step c) is added dropwise over about 1 hour as a solution in an organic solvent comprising hexanes and dichloromethane. Preferably, the reaction mixture is maintained at a temperature of about 0° C. (±5° C.) throughout the addition of the thiol reagent, and may be maintained at about 0° C. for some period of time after addition. The reaction mixture may then be brought to about room temperature and stirred for an appropriate amount of time to complete the reaction.

In a specific embodiment, the thiol solution is added dropwise over about 1 hour at about 0° C. and is maintained at that temperature for about 30 minutes following the addition, then the reaction mixture is gradually warmed to room temperature and is stirred for an additional 2-4 hours.

The invention further provides the optimized ratio of the components in the one-pot two-step process. It will be understood by those of skill in the art that the theoretical stoichiometry of N-(trimethylsilyl)imidazole:sulfur dichloride:thiol reagent is 2:1:2 in order to obtain the desired products. However, in practice, it may be desirable to vary the molar ratio of the various reagents to drive certain reactions to completion, to prevent the formation of by-products, or to facilitate purification, etc. For example, in the route reported previously, N-(trimethylsilyl)imidazole:sulfur dichloride:thiol reagent were used in a molar ratio of about 1.67:1.0:1.6 for the preparation of fluorapacin on an approximately hundred gram scale, and the fluorapacin product required purification by flash chromatography before crystallization. See, e.g., U.S. Ser. No. 11/110,203 (published as US 2005/0261321 now allowed).

In some embodiments, the solution in step a) has a concentration of N-(trimethylsilyl)imidazole of about 1.0 moles/L to about 2.2 moles/L. Preferably, the concentration of step a) is from about 1.6 moles/L to about 2.2 moles/L.

In the present invention, the ratio has been further optimized to facilitate reaction on kilogram to multi-kilogram scale. In some embodiments, N-(trimethylsilyl)imidazole in step a) is provided in a ratio of about 1.8 to about 2.3 molar equivalents relative to the amount of sulfur dichloride in step b). In more preferred embodiments, the N-(trimethylsilyl)imidazole in step a) is provided in a ratio of about 1.9 to about 2.1 molar equivalents relative to the amount of sulfur dichloride in step b). In preferred embodiments, the thiol reagent in step c) is provided in a ratio of about 1.8 to about 2.3 molar equivalents relative to the amount of sulfur dichloride in step b). In more preferred embodiments, the thiol reagent in step c) is provided in a ratio of about 1.9 to about 2.1 molar equivalents relative to the amount of sulfur dichloride in step b). In a particularly preferred embodiment, both the N-(trimethylsilyl)imidazole and the thiol reagent are provided in a ratio of about 1.9 to about 2.1 molar each equivalents relative to the amount of sulfur dichloride in step b).

Steps a) to c) of the processes described above may be conducted using standard equipment known to those of skill in the art. For example, intermediate scale preparations may be conducted using a 5 or 10 L, three-necked round-bottom flask or S212B reactor with cooling and stirring capacity equipped with mechanical stirrer, dropping funnel and nitrogen inlet. Larger reactors, such as 50 L or 100 L reactors may also be used for the preparation of larger scale batches of the trisulfides of the present invention. In specific embodiments, steps a) to c) are conducted using mechanical stirring and under an inert atmosphere, typically using nitrogen gas.

In some embodiments, the process for the preparation of a product of formula (I) or (II), further comprises an isolation step d), wherein step d) comprises filtration of the reaction mixture, for example through Celite or sintered glass, and/or an aqueous extractive workup. In a specific embodiment, following filtration through Celite, the filtrate is washed with one or more aqueous solutions, e.g., water, aqueous sodium bicarbonate solution, water, and brine. Step d) may further comprise drying the organic layer over a drying agent (such as anhydrous $Na_2SO_4$), filtration, and concentration to dryness prior to purification.

In some embodiments, the processes further comprise a purification step e), wherein step e) comprises recrystallization of the isolated product from step d) from at least one crystallization solvent, wherein the product of formula (I) or formula (II) is a crystalline product. In some embodiments, the at least one crystallization solvent comprises or consists of a $C_5$-$C_{10}$ saturated hydrocarbon solvent or mixture thereof; preferably, it is hexanes. The improved purification processes described herein, using a two-stage recrystallization with two quite different solvents avoids the need for chromatography to purify the product that was previously used, and provides a higher purity product in good yield.

In some embodiments, step e) comprises recrystallization from a first crystallization solvent, followed by recrystallization from a second crystallization solvent. In some embodiments, the first crystallization solvent comprises a hydrocarbon solvent and the second crystallization solvent comprises an alcohol solvent, e.g. a C1-C4 alcohol. In a specific embodiment, the first crystallization solvent is hexanes and the second crystallization solvent is anhydrous ethanol. In some embodiments, the second crystallization is conducted under conditions of constant temperature and constant humidity.

In some embodiments, the processes described herein require isolation of a crystalline product, for example from a recrystallization step. In such embodiments, the crystalline product may be isolated, e.g., by filtration or decanting any organic solvent. Conveniently, the crystalline products described herein are isolated by filtration.

The crystallization steps may be performed at room temperature or with mild heating if required for dissolution of the isolated product from step d). If heating is required, preferably it is conducted at a temperature less than or equal to about 60° C. (i.e., ≦60° C.). The heated solution may be filtered, for example, through Celite and/or sintered glass to remove particulate material. Frequently, the solution is allowed to cool gradually to room temperature (if heating was required) and let stand at room temperature for about 12 hours to about 36 hours, preferably about 24 hours, or until a desired amount of crystallization occurs. In some cases, it may be desirable to maintain the solution at a temperature between about −15° C. and about 25° C. until crystallization occurs, preferably between about 0° C. and about 25° C. until crystallization occurs.

The dissolved material may also be treated with decolorizing charcoal and filtered to remove colored impurities prior to crystallization. In some cases, seed crystals may be added to facilitate the crystallization step. The crystalline products from each recrystallization step may be dried under vacuum to lower residual solvent levels. Drying under vacuum may be conveniently conducted at room temperature, or with mild heating, for example at a temperature of ≦40° C. Sometimes, the crystalline products are dried under vacuum at room temperature for about 24 hours. This method provided an ultra-pure product that can be used as a drug standard or for clinical trials.

The anticancer drug fluorapacin, bis(4-fluorobenzyl) trisulfide, was synthesized according to the synthetic route and the technological process (FIG. 1) as described above.

Purification Process of Product

Figure 2:
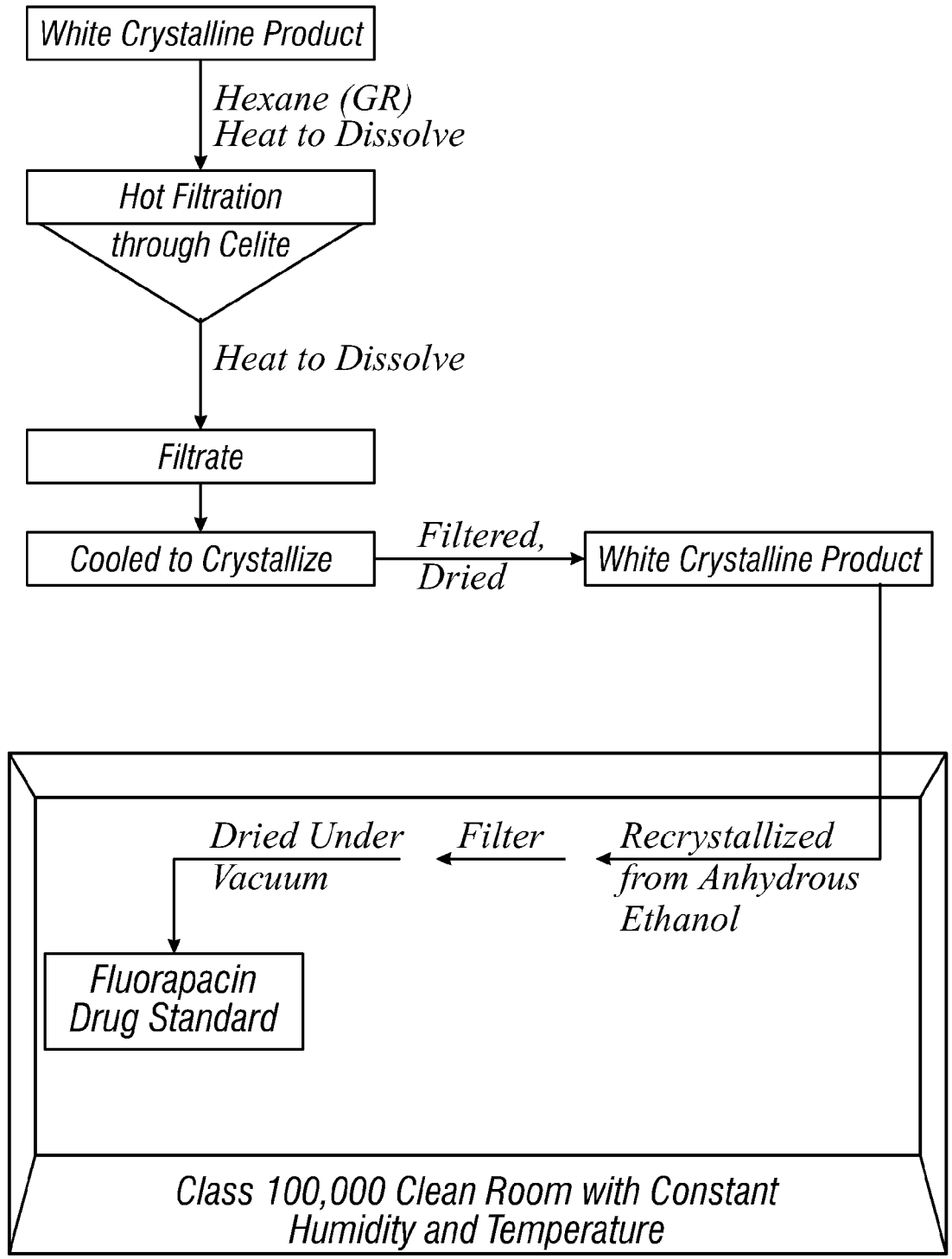
FIG. 2 shows a schematic representation of the purification and refinement process for the preparation of a fluorapacin drug standard.
Figure 3:
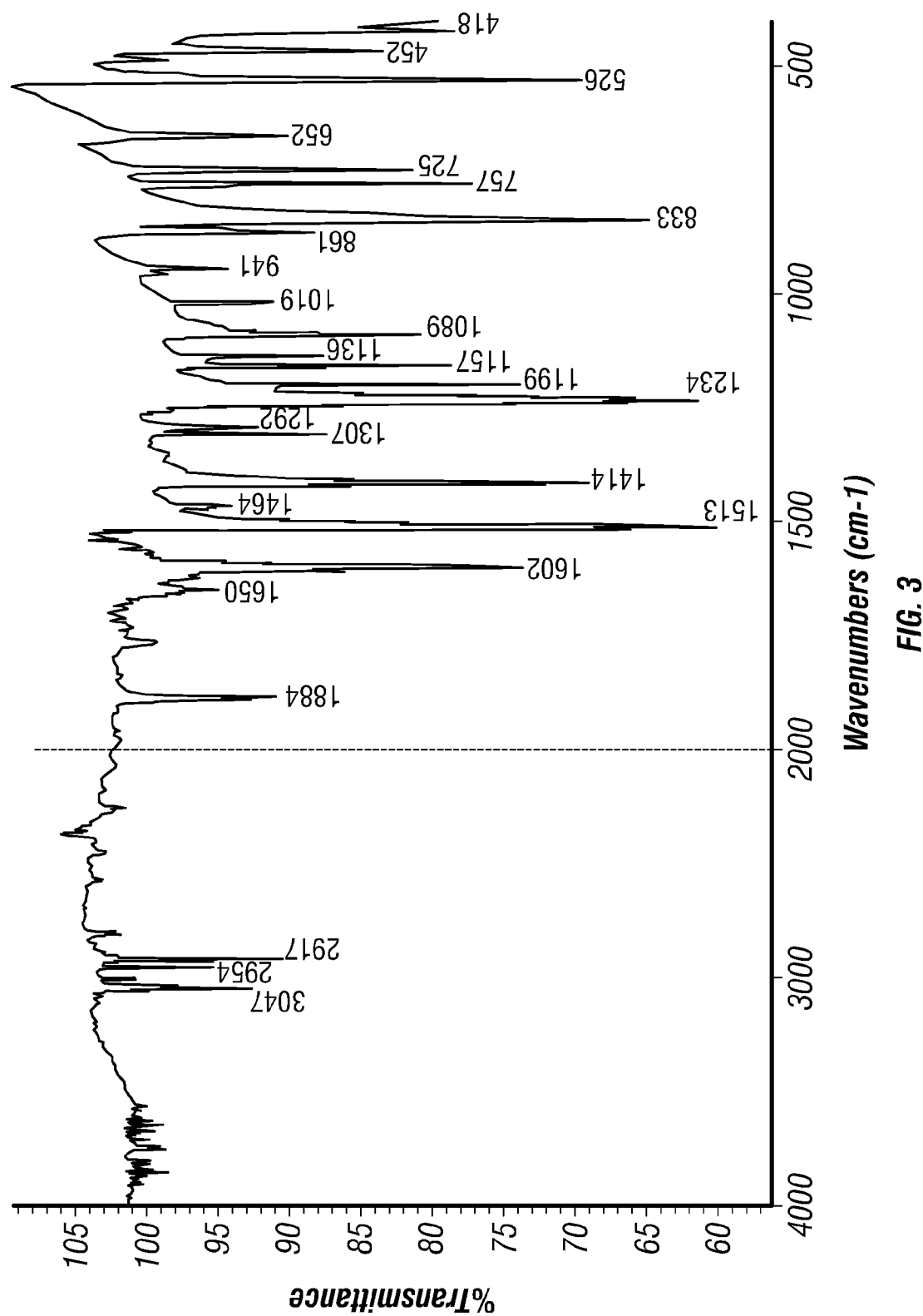
FIG. 3 shows an FT-IR spectrum of fluorapacin.
Figure 4:
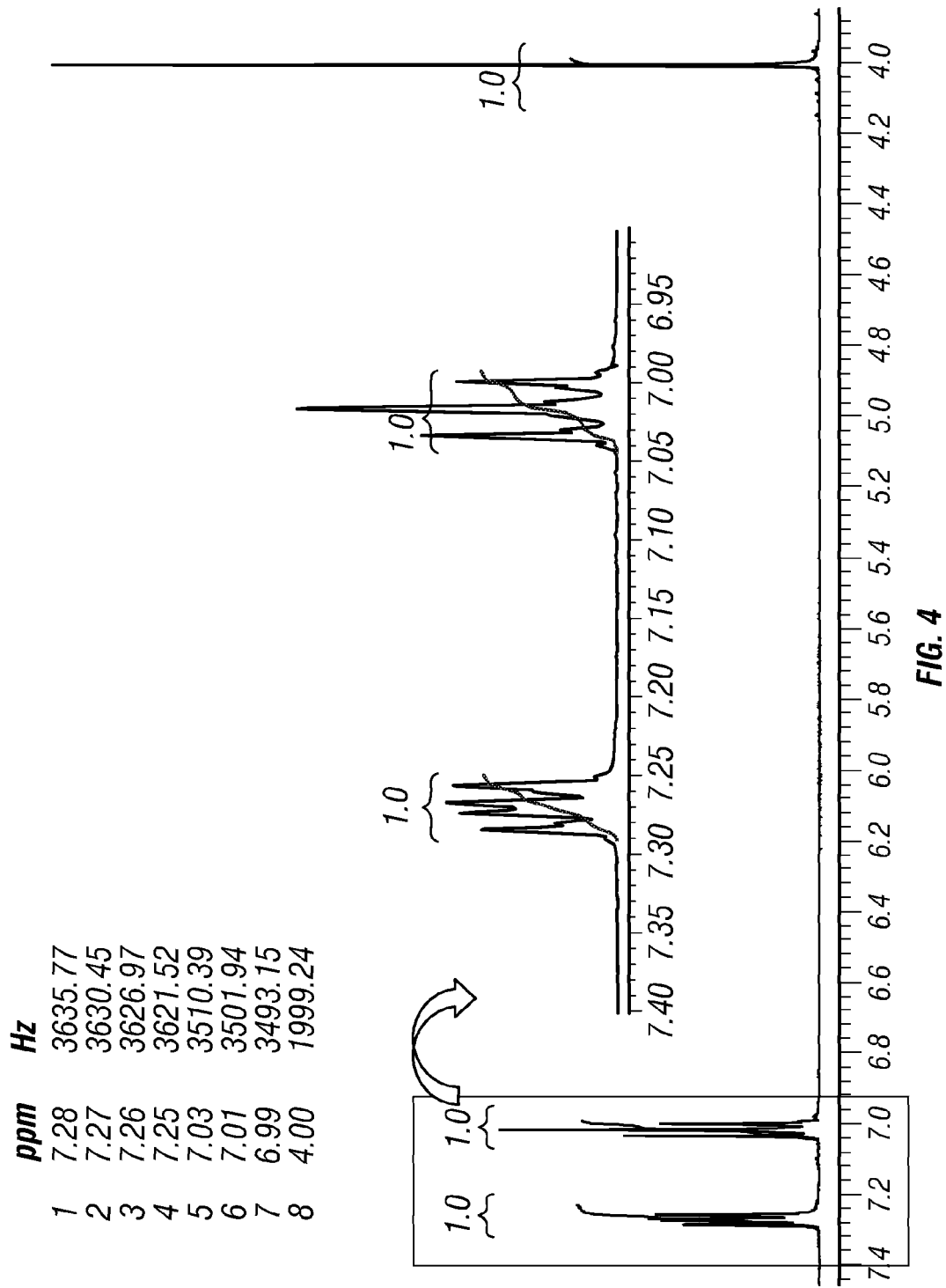
FIG. 4 shows $^1H$ NMR spectrum of fluorapacin.
Figure 5:
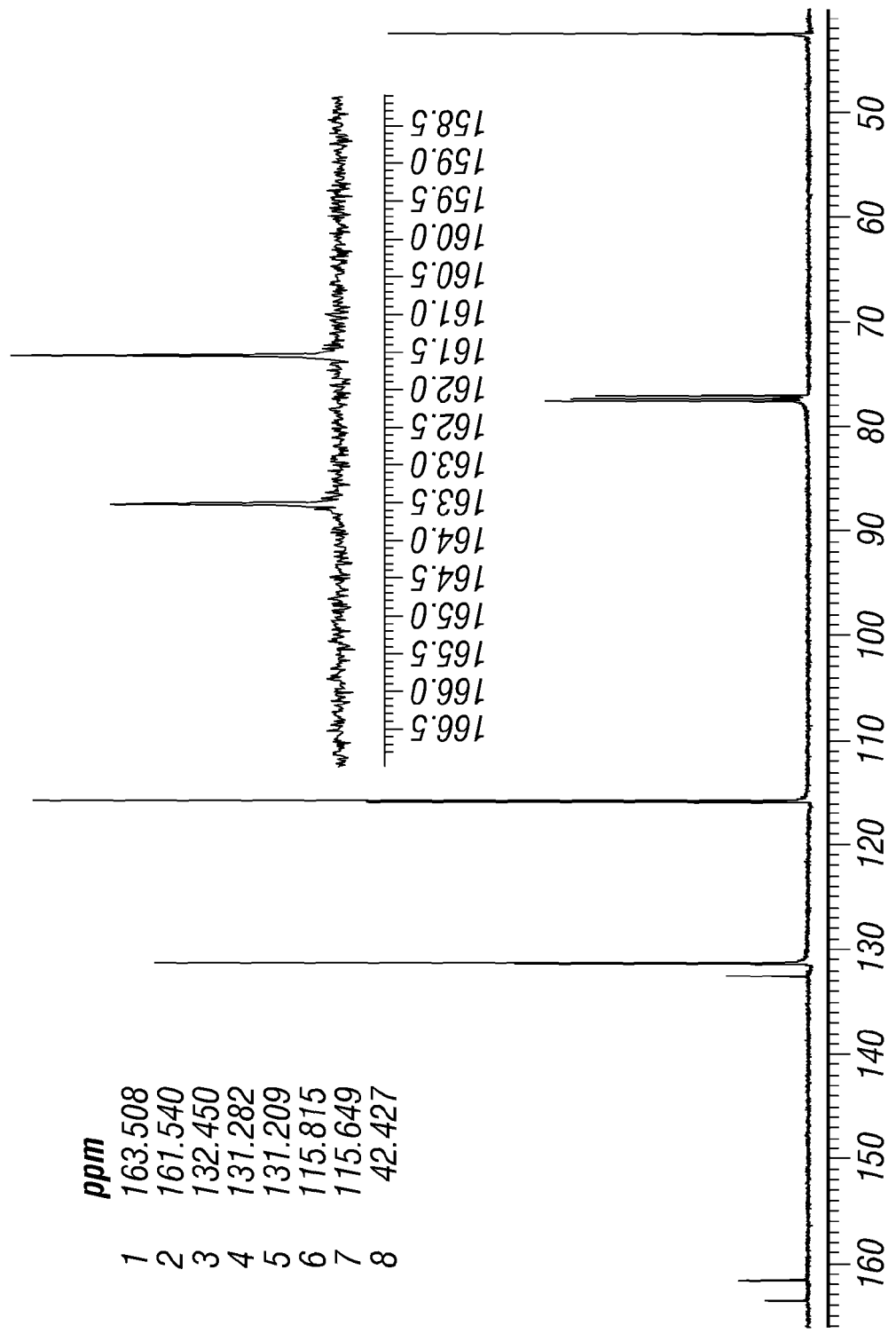
FIG. 5 shows $^{13}C$ NMR spectrum of fluorapacin.
Figure 6:
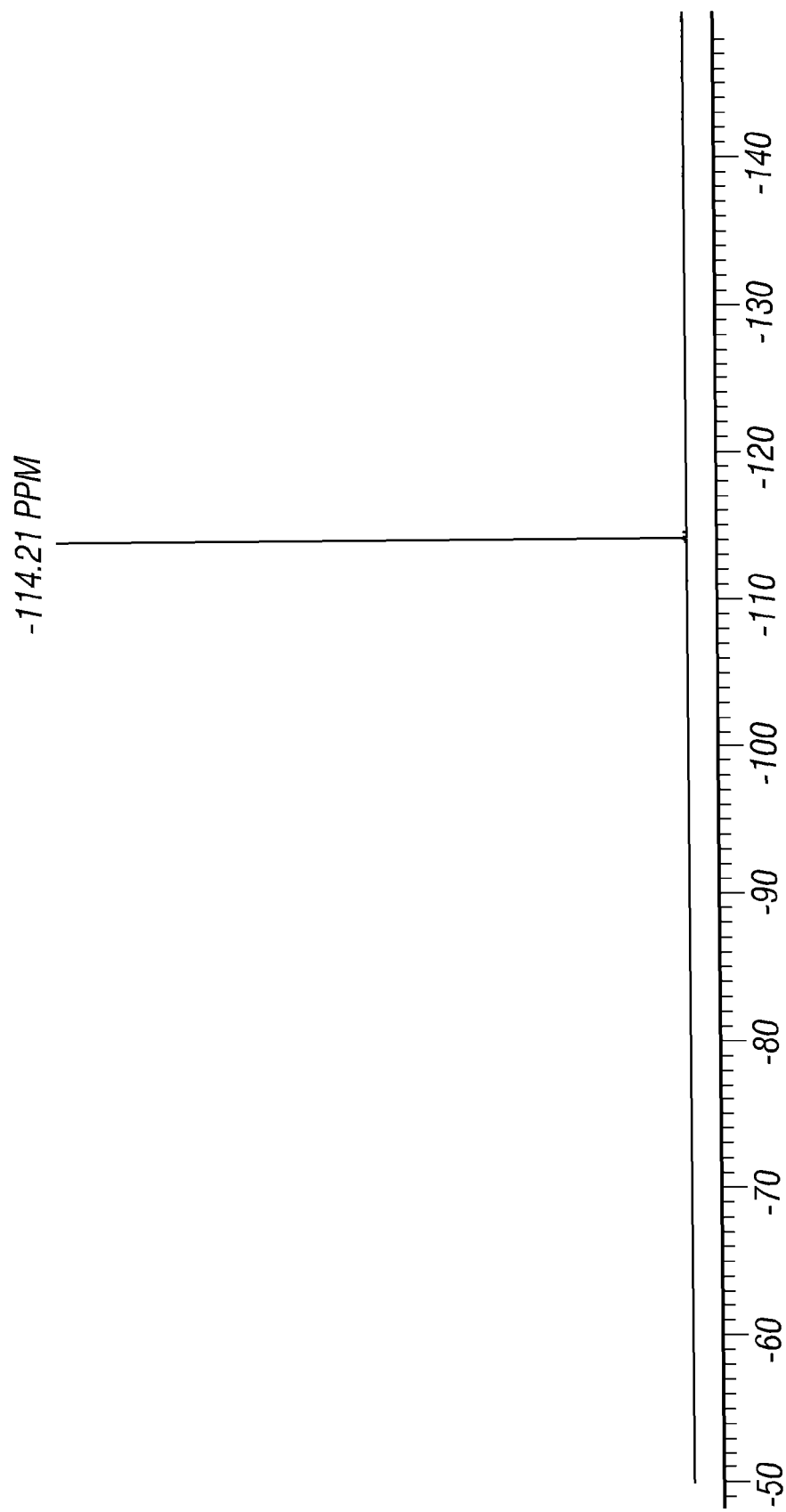
FIG. 6 shows $^{19}F$ NMR spectrum of fluorapacin.

The white crystalline product obtained as described above may be further purified based on the technological process shown in FIG. 2.

In a further aspect, the invention provides a process for preparing crystalline fluorapacin having ≧98% purity, said process comprising:
a) dissolving crystalline fluorapacin in hexanes at a temperature ≦60° C. to provide a hot solution;
b) filtration of the hot solution (e.g., through Celite) to give a filtrate, and warming the filtrate if necessary to provide a clear solution;
c) maintaining the solution at a desired temperature until crystallization occurs, to provide a crystalline product; and
d) isolation of the crystalline product (e.g., by filtration), to provide crystalline fluorapacin having ≧98% purity.

In some embodiments, step a) is conducted at a temperature ≧25° C. and ≦60° C. In other embodiments, step a) is conducted at a temperature between about 35° C. and 60° C.

In some embodiments, the filtrate in step b) is warmed to a temperature ≦60° C. to provide a clear solution. In other embodiments, the filtrate in step b) is warmed to a temperature ≦50° C., sometimes ≦40° C., and sometimes ≦30° C. to provide a clear solution. In some embodiments, no additional warming is required In some embodiments, the solution in step c) is maintained at about room temperature until crystallization occurs. In some such embodiments, the solution is maintained at the selected temperature for about 12 hours to about 36 hours, preferably about 24 hours. In a specific embodiment, the solution is maintained at room temperature for about 24 hours.

In other embodiments, the solution in step c) is maintained at a temperature below room temperature until crystallization occurs, typically for about 12 hours to about 36 hours, preferably about 24 hours. Sometimes, the solution in step c) is maintained at an essentially constant temperature that is ≦25° C. By constant temperature is meant a temperature that doesn't vary by more than about ±5° C. Frequently, the constant temperature ≦25° C. is selected such that it is ≧−15° C., preferably ≧0° C., more preferably ≧15° C. (i.e., the constant temperature is selected in the range between about −15° C. to about 25° C.).

In some embodiments, the process further comprises:
e) recrystallization of the crystalline fluorapacin from step d) from anhydrous ethanol to provide a crystalline product; and
f) isolation of the crystalline product (e.g., by filtration), to provide crystalline fluorapacin having ≧99.5% purity.

In some embodiments, the recrystallization in step e) is conducted using hot anhydrous ethanol, preferably at a temperature of ≦60° C., and the hot solution is gradually cooled to room temperature and let stand at room temperature for a sufficient amount of time for crystallization to occur. In some embodiments, the recrystallization in step e) is conducted under conditions of constant humidity and constant temperature. In certain embodiments, the crystallization process in step e) is conducted at room temperature, under conditions of constant humidity and constant temperature in a class 100,000 clean room. In a preferred embodiment, the crystallization process in step e) is conducted using hot anhydrous ethanol at a temperature of ≦60° C., and the hot solution is gradually cooled to room temperature and let stand at room temperature, under conditions of constant humidity and constant temperature in a class 100,000 clean room.

In some embodiments, the crystalline product isolated in step d) and/or step f) is collected by filtration, for example or similar methods, and is then dried under vacuum, frequently at a temperature of about room temperature.

In another aspect, the invention provides a process for preparing a fluorapacin drug standard, said process comprising:
a) dissolving crystalline fluorapacin in hexanes at a temperature ≦60° C. to provide a hot solution;
b) filtration of the hot solution (e.g., through Celite) to provide a filtrate, and warming the filtrate if necessary to provide a clear solution;
c) maintaining the solution at a desired temperature until crystallization occurs to provide a crystalline product;
d) isolation of the crystalline product (e.g., by filtration), to provide crystalline fluorapacin having ≧98% purity;
e) recrystallization of the crystalline fluorapacin from step d) from hot anhydrous ethanol and then gradually cooled to room temperature, preferably under conditions of constant humidity and constant temperature, and optionally in a class 100,000 clean room, to provide a crystalline product; and
f) isolation of the crystalline product (e.g., by filtration), to provide the fluorapacin drug standard having >99% or ≧99.5% purity.

In some embodiments, the recrystallization in step e) is conducted using hot anhydrous ethanol at a temperature of ≦60° C., and the hot solution is gradually cooled to room temperature and let stand at room temperature for a sufficient amount of time for crystallization to occur.

In some embodiments, the crystalline product isolated in step d) and/or step f) is dried under vacuum, frequently at a temperature of about room temperature. In a specific embodiment, the crystalline product isolated in step d) and/or step f) is dried under vacuum at room temperature for about 24 hours.

In another aspect, the invention provides crystalline fluorapacin having ≧98% purity, >99% purity, or preferably ≧99.5% purity, prepared according to one or more of the processes described herein.

The technological processes described in this invention were successfully applied to the large scale synthesis of bis (4-fluorobenzyl)trisulfide, fluorapacin. The present processes are particularly advantageous on large scale as it allows the avoidance of chromatography which is time consuming and difficult to accomplish on large scale. The process is also advantageous because they allow the rapid purification of fluorapacin and related trisulfide derivatives, which are often susceptible to decomposition upon prolonged handling or manipulation in an impure form.

The reactions described herein may be monitored by thin layer chromatography (TLC) for the disappearance of starting material(s) and/or the appearance of product. Reactions may also be monitored by other standard analytical techniques known to those of skill in the art, including for example, HPLC, LC-MS, GC, GC-MS, and the like. The purity of the products obtained is conveniently assessed by HPLC using a normalization method or an external standard method. However, other methods may be suitable. Unless otherwise indicated, the purities described herein were determined by HPLC.

Applicability of the Technological Process for the Synthesis of Other Trisulfide Derivatives The technological process is also widely applicable to the large scale synthesis of other symmetric trisulfide derivatives of Formula I as long as the substituents on the aryl or aromatic or heterocylic moieties are not nucleophilic or do not react with the sulfur-transferring reagent diimidazolylsulfide. For example, such substituents on the benzyl or aryl or aromatic or heterocyclic methyl moieties can include F, Cl, Br, I, —CONRR', —OR", —SR, —SO$_2$R, —SO$_2$NRR', —NRSO$_2$NRR', —NRC(O)R, —NRC(O)OR", —COOR", —C(O)R, and the like, wherein each R and R' represents H or a substituted or unsubstituted C1-C6 alkyl, and R and R' of any NRR' can cyclize together to form a 5-6 membered ring, and each R" represents a substituted or unsubstituted C1-C6 alkyl, or a C1-C6 alkyl, or C2-C6 alkenyl or alkynyl, heterocycle and others, and these substituents can be attached at any position or any combination of the available positions, if there are two or more such substituents, on the benzyl, aryl, aromatic, fused benzyl, fused aryl, fused aromatic, heterocycle, or fused heterocycle moieties. Such trisulfide derivatives can all be synthesized in large scale by utilizing the technological process described in this invention.

The following Examples are offered to illustrate but not to limit the invention.

EXAMPLE 1

Detailed Technological Process for the Synthesis of Fluorapacin

Starting Materials and Reagents:

The starting materials and reagents used for the synthesis of fluorapacin are listed in Table 1.

TABLE 1

Starting Materials and Reagents

| Description | Quantity (volume, ml) | mole |
| --- | --- | --- |
| N-trimethylsilylimidazole, d = 0.956 | 643.5 | 4.386 |
| Sulfur dichloride, d = 1.621 | 139.4 | 2.194 |
| 4-fluorobenzyl mercaptan, d = 1.157 | 529 | 4.218 |
| Hexane | 1750 | — |
| Methylene chloride | 700 | — |

Detail Technological Procedure:
1) 5 or 10 L, three-necked round-bottom flask or S212B reactor with cooling and stirring capacity was equipped with mechanical stirrer, dropping funnel and nitrogen inlet. Anhydrous hexane (1500 mL, dried via molecular sieve) and anhydrous methylene chloride (500 mL, dried via molecular sieve) were added to the reactor. N-Trimethylsilylimidazole (634.5 mL, 4.386 mol) was added and mixed well by stirring. Sulfur dichloride (139.4 mL, 2.194 mol) was added dropwise over a period of 1 h at room temperature under a nitrogen atmosphere and stirring. A white precipitate was formed. The reaction mixture was stirred for an additional hour.
2) The reaction mixture was cooled to 0° C. under a nitrogen atmosphere. A solution of 4-fluorobenzyl mercaptan (529 mL, 4.218 mol) in 250 mL of anhydrous hexane and 200 mL of methylene chloride was added dropwise over a period of 1 h under stirring and nitrogen atmosphere. The resulting reaction mixture was stirred at 0° C. for 30 min, and then the cooling bath (or system) was removed to allow the temperature rising to room temperature while the reaction mixture was stirred. The total stirring time after the addition of 4-fluorobenzyl mercaptan was completed was approximately 3 hours. The reaction was monitored by TLC (hexane-ethyl acetate: 40:1, R$_f$=0.45).
3) The white to pale yellow solid formed was filtered off through a pad of Celite and washed with small amount of hexanes.
4) The filtrate was washed with water (2000 mL), 1% aqueous sodium bicarbonate solution (2000 mL), water (2000 mL), and then saturated aqueous sodium chloride solution (2000 mL).
5) The organic layer was dried over anhydrous sodium sulfate. The drying agent was filtered off, and the filtrate was concentrated to dryness under reduced pressure providing pale yellow solid crude product.
6) The resulting crude product (400 g) was re-crystallized from hexanes (3000 mL). The crystalline was filtered and dried under vacuum to give white crystalline product.
7) The white crystalline product thus obtained was recrystallized from anhydrous ethanol (1200 mL) to provide purified fluorapacin product.
8) After drying under vacuum for 24 h, 345.6 g white crystalline product was obtained, yield 52.5%. HPLC purity >99.4% (normalization method); m. p. 60.7-61.9° C.

EXAMPLE 2

Detailed Technological Process for the Synthesis of Fluorapacin

Starting Materials and Reagents:
The starting materials and reagents used for the synthesis of fluorapacin are listed in Table 2.

TABLE 2

Starting Materials and Reagents

| Description | Quantity (volume, ml) | mole |
| --- | --- | --- |
| N-trimethylsilylimidazole, d = 0.956 | 4158 | 27.49 |
| Sulfur dichloride, d = 1.621 | 852 | 13.41 |
| 4-fluorobenzyl mercaptan, d = 1.157 | 3192 | 25.45 |
| Hexane | 18800 | — |
| Methylene chloride | 5300 | — |

Technological Procedure:
1) A 50 L reactor with cooling and stirring capacity was equipped with mechanical stirrer, dropping funnel and nitrogen inlet. Anhydrous hexane (18800 mL, dried via molecular sieve) and anhydrous methylene chloride (5300 mL, dried via molecular sieve) were added to the reactor. N-Trimethylsilylimidazole (4158 mL, 27.49 mol) was added and mixed well by stirring. Sulfur dichloride (582 mL, 13.41 mol) was added dropwise over a period of 1 h at room temperature under a nitrogen atmosphere and stirring. The white precipitate was formed. The reaction mixture was stirred for an additional hour.
2) The reaction mixture was cooled to 0° C. under a nitrogen atmosphere. A solution of 4-fluorobenzyl mercaptan (3192 mL, 25.45 mol) in 1800 mL of anhydrous hexane and 1300 mL of methylene chloride was added dropwise over a period of 1 h under stirring and nitrogen atmosphere. The resulting reaction mixture was stirred at 0°

C. for 30 min, and then the cooling bath (or system) was removed to allow the temperature rising to room temperature while the reaction mixture was stirred. The total stirring time after the addition of 4-fluorobenzyl mercaptan was completed was approximately 3 hours. The reaction was monitored by TLC (hexane-ethyl acetate: 40:1, $R_f$=0.45).

3) The solid material formed was filtered off through a pad of Celite and washed with small amount of hexanes.
4) The filtrate was washed with water (10000 mL), 1% aqueous sodium bicarbonate solution (10000 mL), water (10000 mL), and then saturated aqueous sodium chloride solution (10000 mL).
5) The organic layer was dried over anhydrous sodium sulfate. The drying agent was filtered off, and the filtrate was concentrated to dryness under reduced pressure providing pale yellow solid crude product.
6) The resulting crude product (3071.7 g) was re-crystallized from hexanes (16000 mL). The crystalline was filtered and dried under vacuum to give white crystalline product.
7) The white crystalline product thus obtained was recrystallized from anhydrous ethanol (8000 mL) to provide purified fluorapacin product.
8) After dried under vacuum for 24 h, 2537 g white crystalline product was obtained, yield 63.4%. HPLC purity 99.98% (normalization method); m. p. 61.0-62.1° C.

EXAMPLE 3

Detailed Technological Process for the Synthesis of Fluorapacin

Starting Materials and Reagents:

The starting materials and reagents used for the synthesis of fluorapacin are listed in Table 3.

TABLE 3

Starting Materials and Reagents

| Description | Quantity (volume, ml) | mole |
|---|---|---|
| N-trimethylsilylimidazole, d = 0.956 | 8880 | 60.52 |
| Sulfur dichloride, d = 1.621 | 1775 | 27.98 |
| 4-fluorobenzyl mercaptan, d = 1.157 | 6718 | 54.66 |
| Hexane | 36000 | — |
| Methylene chloride | 11000 | — |

Technological Procedure:
1) An 100 L reactor with cooling and stirring capacity was equipped with mechanical stirrer, dropping funnel and nitrogen inlet. Anhydrous hexane (36000 mL, dried via molecular sieve) and anhydrous methylene chloride (11000 mL, dried via molecular sieve) were added to the reactor. N-Trimethylsilylimidazole (8880 mL, 62.52 mol) was added and mixed well by stirring. Sulfur dichloride (1775 mL, 27.98 mol) was added dropwise over a period of 1 h at room temperature under a nitrogen atmosphere and stirring. The white precipitate was formed. The reaction mixture was stirred for an additional hour.
2) The reaction mixture was cooled to 0° C. under a nitrogen atmosphere. A solution of 4-fluorobenzyl mercaptan (6718 mL, 54.66 mol) in 300 mL of anhydrous hexane and 200 mL of methylene chloride was added dropwise over a period of 1 h under stirring and nitrogen atmosphere. The resulting reaction mixture was stirred at 0° C. for 30 min, and then the cooling bath (or system) was removed to allow the temperature to rise to room temperature while the reaction mixture was stirred. The total stirring time after the addition of 4-fluorobenzyl mercaptan was completed was approximately 3 hours. The reaction was monitored by TLC (hexane-ethyl acetate: 40:1, $R_f$=0.45).

3) The solid material formed was filtered off through a pad of Celite and washed with a small amount of hexanes.
4) The filtrate was washed with water (10000 mL), 1% aqueous sodium bicarbonate solution (10000 mL), water (10000 mL), and then saturated aqueous sodium chloride solution (10000 mL).
5) The organic layer was dried over anhydrous sodium sulfate. The drying agent was filtered off, and the filtrate was concentrated to dryness under reduced pressure providing pale yellow solid crude product.
6) The resulting crude product (6500 g) was re-crystallized from hexanes (20000 mL). The crystalline was filtered and dried under vacuum to give white crystalline product.
7) The white crystalline product thus obtained was recrystallized from anhydrous ethanol (13500 mL) to provide purified fluorapacin product.
8) After drying under vacuum for 24 h, 3343 g white crystalline product was obtained, yield 50.5%. HPLC purity 99.92% (normalization method); m. p. 60.5-62.0° C.

EXAMPLE 4

Process for the Preparation of Fluorapacin Drug Standard

White crystalline fluorapacin (30 g) was dissolved in 250 mL of hexane (GR) at a temperature ≦60° C. The hot solution was filtered through Celite, and the filtrate was warmed to clear solution which was kept for 24 hours for crystallization. The white crystalline product was filtered and dried under vacuum at room temperature providing fluorapacin as a crystalline product (HPLC purity: ≧99.5%).

A portion of the crystalline product was recrystallized from anhydrous ethanol at a temperature ≦60° C. in a Class 100,000 environment under conditions of constant humidity and temperature (rt). The crystalline product was filtered and dried under vacuum at room temperature for 24 h providing desired white crystalline product as fluorapacin standard sample, HPLC purity 99.856% (external standard method); m. p. 61.1-62.2° C.

EXAMPLE 5

Structural Characterization of Fluorapacin

Figure 7:
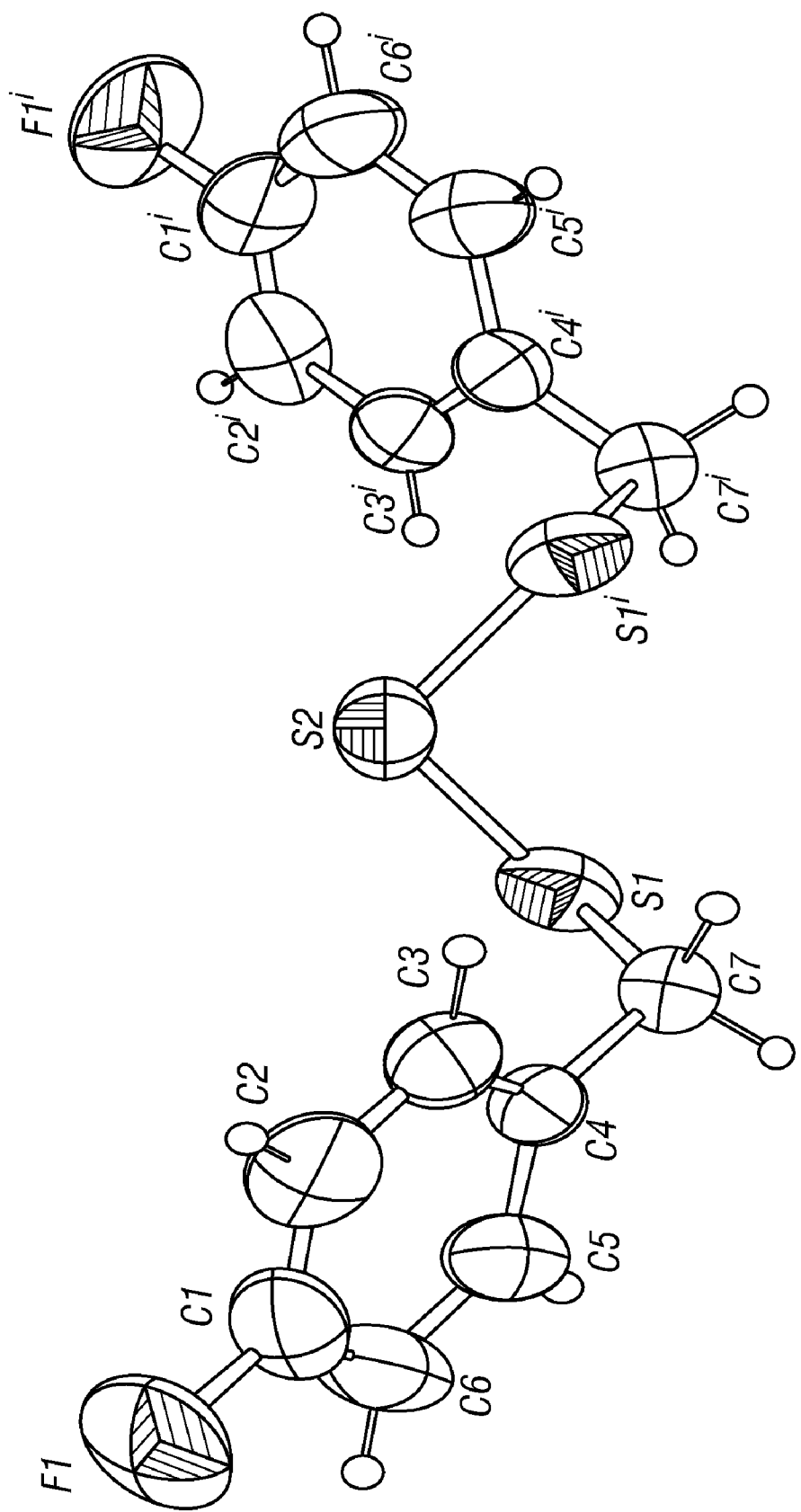
FIG. 7 shows an ORTEP representation of the single crystal molecular configuration of fluorapacin.

The structure of fluorapacin drug substance thus synthesized by the technological process of the present invention was fully characterized by elemental analysis, $^1$H NMR, $^{13}$C NMR, $^{19}$F NMR, mass (EI-MS), FT-IR, and UV-V is spectrometric analyses. The infrared (IR) and $^1$H, $^{13}$C and $^{19}$F NMR spectra of fluorapacin are provided in FIGS. 3-6, respectively. An ORTEP representation of the single crystal molecular configuration of fluorapacin is provided in FIG. 7.

The crystalline products provided by the processes described herein were also characterized by differential scanning calorimetry (DSC) and thermogravimetry (TG) analyses; single crystal X-ray diffraction (SXRD), and other methods. These data compared favorably to the information generated for fluorapacin published previously. See An, H.; Zhu, J.; Wang, X.-B.; Xu, X. Synthesis and anti-tumor evaluation of new trisulfide derivatives, *Bioorg. Med. Chem. Lett.* (2006), 16: 4826-4829; see also An, H.; Hu, X.-R.; Gu, J.-M.; Chen, L.-S.; Xu, W.-M.; Mo, X.-P.; Xu, W.-H.; Wang, X.-B.; Xu, X. "Crystal structure determination of new antimitotic agent bis(p-fluorobenzyl)trisulfide", *AAPS PharmSciTech*, (2008), 9:551-556.

The invention claimed is:

1. A process for preparing a product of formula (I),

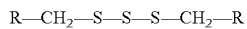 (I)

said process comprising:
a) providing a solution of N-(trimethylsilyl)imidazole in an organic solvent;
b) adding neat sulfur dichloride to said solution to provide a reaction mixture comprising diimidazolylsulfide; and
c) without isolation, contacting the diimidazolylsulfide with a thiol reagent of formula RCH$_2$SH to provide the product of formula (I);
d) isolation of the product of formula (I); and
e) purification of the isolated product by recrystallization from at least one crystallization solvent, wherein the product of formula (I) is a crystalline product; and
wherein R is an optionally substituted aryl or an optionally substituted heteroaryl group.

2. The process of claim 1, wherein each R group is an optionally substituted phenyl.

3. The process of claim 1, wherein each R group is (4-fluoro)phenyl.

4. A process for preparing a product of formula (II),

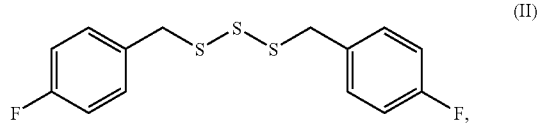

said process comprising:
a) providing a solution of N-(trimethylsilyl)imidazole in an organic solvent;
b) adding neat sulfur dichloride to said solution to provide a reaction mixture comprising diimidazolylsulfide;
c) without isolation, contacting the diimidazolylsulfide with a thiol reagent of formula (4-F—C$_6$H$_4$)CH$_2$SH, to provide the product of formula (II);
d) isolation of the product of formula (II); and
e) purification of the isolated product by recrystallization from at least one crystallization solvent, wherein the product of formula (II) is a crystalline product; and
wherein the crystalline product has ≧98% purity.

5. The process of claim 4, wherein the organic solvent in step a) comprises a halogenated solvent.

6. The process of claim 4, wherein the organic solvent in step a) comprises a mixture of hexanes and dichloromethane.

7. The process of claim 4, wherein the organic solvent in step a) is a mixture of hexanes and dichloromethane having a ratio of about 3:1.

8. The process of claim 4, wherein the neat sulfur dichloride in step b) is added over about 1 hour at room temperature.

9. The process of claim 4, wherein step c) further comprises cooling the reaction mixture to about 0° C. prior to contacting the diimidazolylsulfide with the thiol reagent.

10. The process of claim 4, wherein the thiol reagent in step c) is provided as a solution in an organic solvent.

11. The process of claim 4, wherein the thiol reagent in step c) is added over about 1 hour as a solution in an organic solvent comprising hexanes and dichloromethane.

12. The process of claim 9, wherein the reaction mixture is maintained at a temperature of about 0° C. while the thiol reagent is added over about 1 hour as a solution in an organic solvent comprising hexanes and dichloromethane.

13. The process of claim 4, wherein the N-(trimethylsilyl)imidazole in step a) is provided in a ratio of about 1.8 to about 2.3 molar equivalents relative to the amount of sulfur dichloride in step b).

14. The process of claim 4, wherein the N-(trimethylsilyl)imidazole in step a) is provided in a ratio of about 1.9 to about 2.1 molar equivalents relative to the amount of sulfur dichloride in step b).

15. The process of claim 4, wherein the thiol reagent in step c) is provided in a ratio of about 1.8 to about 2.3 molar equivalents relative to the amount of sulfur dichloride in step b).

16. The process of claim 4, wherein the thiol reagent in step c) is provided in a ratio of about 1.9 to about 2.1 molar equivalents relative to the amount of sulfur dichloride in step b).

17. The process of claim 4, wherein step d) comprises filtration of the reaction mixture and an aqueous extractive workup.

18. The process of claim 4 wherein the at least one crystallization solvent is hexanes.

19. The process of claim 18 wherein the isolated product from step d) is dissolved in hexanes at a temperature ≦60° C. to provide a hot solution, the hot solution is filtered to provide a filtrate, and the filtrate is maintained at room temperature until crystallization occurs to provide a crystalline product.

20. A process for preparing crystalline fluorapacin having ≧98% purity, said process comprising:
a) dissolving crystalline fluorapacin in hexanes at a temperature ≦60° C. to provide a hot solution;
b) filtration of the hot solution to give a filtrate, and warming the filtrate if necessary to provide a clear solution;
c) maintaining the solution at a desired temperature until crystallization occurs, to provide a crystalline product;
d) isolation of the crystalline product, to provide crystalline fluorapacin having ≧98% purity.

21. The process of claim 20, wherein step a) is conducted at a temperature ≧25° C. and ≦60° C.

22. The process of claim 20, wherein the solution in step c) is maintained at about room temperature for about 24 hours.

23. The process of claim 20, further comprising:
e) recrystallization of the crystalline fluorapacin from step d) from hot anhydrous ethanol at a temperature ≦60° C. and gradually cooled to room temperature to provide a crystalline product; and
f) isolation of the crystalline product, to provide crystalline fluorapacin having ≧99.5% purity.

24. The process of claim 23, wherein step e) is conducted under conditions of constant humidity and constant temperature.

25. A process for preparing a fluorapacin drug standard, said process comprising:

a) dissolving crystalline fluorapacin in hexanes at a temperature $\leq 60°$ C. to provide a hot solution;

b) filtration of the hot solution to provide a filtrate, and warming the filtrate if necessary to provide a clear solution;

c) maintaining the solution at a desired temperature until crystallization occurs to provide a crystalline product;

d) isolation of the crystalline product, to provide crystalline fluorapacin having $\geq 98\%$ purity;

e) recrystallization of the crystalline fluorapacin from step d) from hot anhydrous ethanol at a temperature $\leq 60°$ C. and gradually cooled to room temperature under conditions of constant humidity and constant temperature to provide a crystalline product; and f) isolation of the crystalline product, to provide the fluorapacin drug standard having $\geq 99.5\%$ purity.

26. The process of claim 25, further comprising drying the crystalline product isolated in step d) and/or step f) under vacuum at room temperature for about 24 hours.

* * * * *